United States Patent
Chevalier et al.

(10) Patent No.: US 7,429,638 B2
(45) Date of Patent: Sep. 30, 2008

(54) HIGH REFRACTIVE INDEX POLYSILOXANES AND THEIR PREPARATION

(75) Inventors: Pierre Maurice Chevalier, Penarth (GB); Duan Li Ou, Framingham, MA (US)

(73) Assignee: Dow Corning Limited, Barry, Wales (GB)

( * ) Notice: Subject to any disclaimer, the term of this patent is extended or adjusted under 35 U.S.C. 154(b) by 243 days.

(21) Appl. No.: 10/486,375

(22) PCT Filed: Jul. 18, 2002

(86) PCT No.: PCT/EP02/08545

§ 371 (c)(1),
(2), (4) Date: Jan. 17, 2004

(87) PCT Pub. No.: WO03/011944

PCT Pub. Date: Feb. 13, 2003

(65) Prior Publication Data

US 2004/0236057 A1 Nov. 25, 2004

(30) Foreign Application Priority Data

Jul. 28, 2001 (GB) .................................. 0118473.8

(51) Int. Cl.
*C08G 77/04* (2006.01)

(52) U.S. Cl. .......................................... 528/43; 528/39

(58) Field of Classification Search ............... 528/39, 528/43

See application file for complete search history.

(56) References Cited

U.S. PATENT DOCUMENTS 2,528,355 A * 10/1950 Dingman et al. ............. 556/489
5,233,007 A 8/1993 Yang
5,260,469 A 11/1993 Swiatek
5,384,383 A 1/1995 Legrow et al.
5,539,137 A 7/1996 Lewis et al.
6,084,050 A 7/2000 Ooba et al.
6,285,513 B1 9/2001 Tsuji et al.
6,361,718 B1 * 3/2002 Shinmo et al. ............. 264/1.21

FOREIGN PATENT DOCUMENTS

| JP | 07-082378 | 3/1995 |
| JP | 11-310755 | 11/1999 |
| JP | 2000-231001 | 8/2000 |
| JP | 2002-235103 | 8/2000 |
| WO | WO 94/08557 | 4/1994 |
| WO | WO 03/011944 A2 | 2/2003 |

OTHER PUBLICATIONS

Derwent Data base XP-002226868, XP-002226869, date unknown.

* cited by examiner

*Primary Examiner*—Kuo-Liang Peng
(74) *Attorney, Agent, or Firm*—Howard & Howard Attorneys, P.C.

(57) ABSTRACT

A polysiloxane having a refractive index of about 1.56 measured at light wavelength 633 nm, characterized in that the polysiloxane includes siloxane T units of the formula

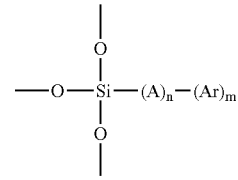

where A represents an alkylene group having 1 to 4 carbon atoms: n=0 or 1; m is at least 1; and Ar is an aryl group substituted by at least one iodine, bromine or chlorine atom, or is a polynuclear aromatic group. The invention includes chlorosilanes having the formula $(Ar)_m-(A)_nSiCl_3$, useful in forming high refractive index polysiloxanes.

30 Claims, No Drawings

HIGH REFRACTIVE INDEX POLYSILOXANES AND THEIR PREPARATION

This invention relates to high refractive index silicone polymers (polysiloxanes) and their manufacture. There is an increasing demand for polymers and resins with higher refractive Index for optical uses.

Two main ways have been described before to enhance the refractive indices of silicone polymers and glasses. The first approach is to blend silica or organopolysiloxane with a refractive index enhancer such as $TiO_2$ or $ZrO_2$ or to react silica or silicone/silicate precursors with titanium alkoxides as described in WO-A-99/19266 or with a $TiO_2$—$ZrO_2$—$SiO_2$—$SnO_2$ composite sol as described as described in WO-A-99/19266. However, the refractive index of the final inorganic material may be lower than expected because of inhomogeneity (scattering effect of oxide particles). Moreover the brittle glass or co-inorganic material is difficult to process and does not always fulfil the mechanical requirements for some optical applications.

A second approach is to prepare phenyl-containing silicones. Phenylalkylsiloxanes have been described allowing tunable refractive index from 1.43 to 1.55, for example in U.S. Pat. No. 5,233,007, WO-A-93/19074, WO-A-94/08557 and U.S. Pat. No. 5,384,383. There is a need for higher refractive index silicones, particularly having a refractive index of above 1.56 measured at light wavelength 633 nm.

JP-A-2000-235103 describes optical elements of refractive index 1.55 or greater consisting of a silicone resin which contains a substituted or unsubstituted aryl or aralkyl group. Examples of aryl groups described are pentachlorophenyl, pyrenyl and tribromophenyl. The aryl groups are generally incorporated as diorganosiloxane (D) units of the formula $Z_2SiO_{2/2}$, where Z is the substituted or unsubstituted aryl group.

U.S. Pat. No. 6,084,050 describes thermo-optic devices composed of heat resistant low loss low birefringence silicone materials which contain a deuterated phenyl group or a halogenated phenyl group.

According to one aspect of the present invention a high refractive index polysiloxane includes siloxane T units of the formula

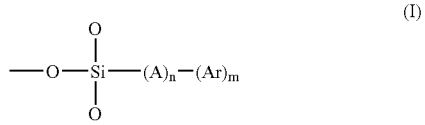

(I)

where A represents an alkylene group having 1 to 4 carbon atoms: n=0 or 1; m is at least 1; and Ar is an aryl group substituted by at least one iodine, bromine or chlorine atom, or is a polynuclear aromatic group.

We have found that polysiloxanes based on such siloxane T units have high refractive index and are readily processable, for example they can be dissolved in an organic solvent and cast and cured on a substrate to form a high refractive index layer on a substrate. Polysiloxanes based on T units generally have a higher refractive index than polysiloxanes based on D units. Whilst it is theoretically possible to include a higher proportion of refractive index-modifying groups in a polysiloxane based on D units, such a polysiloxane cannot readily be processed to form a high refractive index layer on a substrate.

According to another aspect of the invention a process for the preparation of a high refractive index polysiloxane is characterised in that an aryl polysiloxane containing Ar'(R)$xSiO_{3-x/2}$ units, where Ar' is an aryl group; each X independently represents an alkyl, aryl, haloalkyl, alkoxy or hydrogen group; and x=0, 1 or 2 is reacted with chlorine, bromine or iodine.

According to a further aspect of the invention a further process for the preparation of a high refractive index polysiloxane characterised in that an aryl hydrosiloxane resin containing $(Ar)_m$-$(A)_n(R)_xSiO_{3-x/2}$ units and $HsiO_{3/2}$ units, where Ar, A, m and n are defined as in Claim 1; each R independently represents an alkyl, aryl, haloalkyl, alkoxy or hydrogen group or a group of the formula $(AR)_m$-$(A)_n$-; and x=0, 1 or 2; is treated with a base to condense at least some of the $HsiO_{3/2}$ units to form $SiO_{4/2}$ units.

The invention includes new chlorosilanes having the formula (Ar)m-(A) nSiCl3, where Ar, A, m and n are defined as above.

The invention also includes a process for the preparation of a chlorosilane of the formula (Ar)m-(A)n(R')xSiCl(3-x), where Ar, A, m and n are defined as in Claim 1; each R' independently represents an alkyl, aryl, or haloalkyl group; and x=0, 1 or 2; characterised in that an organic chloride of the formula (Ar)m-(A)nCl is reacted with a chlorosilane of the formula H(R')xSiCl(3-x) in the presence of a tertiary amine. Further, the invention includes a process for the preparation of a high refractive index polysiloxane, characterised in that at least one chlorosilane of the formula (Ar)m-(A)n(R')xSiCl(3-x), or at least one chlorosilane of the formula (Ar)m-(A)n(R')xSiCl(3-x) prepared as described above, is hydrolysed and condensed, optionally together with another chlorosilane, in the presence of water and a dipolar aprotic solvent.

In the group (Ar)m-(A)n-, the Ar radical can be an aryl group substituted by at least one iodine, bromine or chlorine atom, for example a substituted phenyl group, or is a polynuclear aromatic group. Examples of substituted aryl groups Ar include iodophenyl, diiodophenyl, bromophenyl, dibromophenyl, chlorophenyl, dichlorophenyl and trichlorophenyl. In general the substitution of iodine in an aryl group has a much greater effect in increasing the refractive index of a polysiloxane containing it than the substitution of bromine, which in turn has a substantially greater effect than the substitution of chlorine. Polysiloxanes in which Ar is a phenyl group substituted by at least one iodine atom are thus particularly preferred. The aryl group of Ar can optionally contain additional substituents, for example one or more alkyl groups such as methyl or ethyl.

The polynuclear aromatic group Ar can be a fused ring aryl group such as an optionally substituted naphthyl, anthracenyl, phenanthrenyl or pyrenyl group, or can be a polynuclear group having non-fused aromatic rings such as an optionally substituted biphenyl group. The group Ar can be a polynuclear aromatic group substituted by at least one iodine, bromine or chlorine atom, for example an iodonaphthyl, chloronaphthyl, bromonaphthyl or (iodophenyl)phenyl group.

The alkylene linkage (A) can be present or absent, i.e. the value of n can be 0 or 1; the group (A) has little effect on the refractive index of the polysiloxane and the presence or absence of the alkylene linkage can be chosen according to the ease of preparation of the corresponding polysiloxane. If present, A is preferably a methylene, ethylidene or ethylene linkage. The value of m is usually 1, although when A is present and particularly when A has more than 1 carbon atom it can be substituted by 2 or more Ar groups.

Examples of suitable groups (Ar)m-(A)n- include 2-iodophenyl, 4-iodophenyl, 2-iodophenylmethyl, 9-anthracenylmethyl, 3,4-diiodophenyl, 5-iodonaphth-1-yl and 4-(3-iodophenyl)phenyl.

The polysiloxane of the invention preferably contains at least 20%, most preferably at least 50%, of the siloxane units of the formula (1). Such units can form up to 90% or even 100% of the polysiloxane. However we have found that the presence of $SiO_{4/2}$ units (Q units) in the polysiloxane confers additional advantages. The presence of Q groups generally confers easier processing, so that the polysiloxane is soluble in organic solvents and can be spin coated on substrates. The processing of a polysiloxane of high aryl content to form a good coated film may be difficult if the polysiloxane does not contain Q groups. The presence of Q groups also improves the thermomechanical properties of the polysiloxane, such as increasing rigidity, particularly at elevated temperature. The level of Q groups in the polysiloxane is preferably at least 5% and most preferably at least 10, for example up to 30 or 40%.

The polysiloxane of the invention can additionally contain diorganosiloxane units (D units) and/or triorganosiloxane units (M units). Such D or M units can in general have the formula $(R)xSiO(4-x/2)$, where each R independently represents an alkyl, aryl, haloalkyl, alkoxy or hydrogen group; and x=2 or 3. Aryl groups R can be unsubstituted aryl groups, for example phenyl groups, or can be aryl groups substituted by at least one iodine, bromine or chlorine atom or polynuclear aromatic groups as defined for Ar above. The polysiloxane can optionally contain monoorganosiloxane units (T units) $RSiO_{3/2}$ in which R is an alkyl, unsubstituted aryl, haloalkyl, alkoxy or hydrogen group.

In one preferred process according to the invention for the preparation of a high refractive index polysiloxane, an aryl polysiloxane containing Ar'(R)xSiO(3-x/2) units, where Ar' is an aryl group; each R independently represents an alkyl, aryl, haloalkyl, alkoxy or hydrogen group; and x=0, 1 or 2 is reacted with chlorine, bromine or iodine. The group Ar' can for example be a phenyl group, for example the aryl polysiloxane can be a phenyl T resin, or a naphthyl, tolyl or xylyl group. If the aryl polysiloxane is a T resin, it can comprise substantially all Ar'SiO3/2 units as in a phenyl T resin, or can be a phenyl alkyl T resin preferably containing at least 50% Ar'SiO3/2 units and up to 50% RSiO3/2 units where R is alkyl, for example a phenyl propyl T resin. Reaction with iodine is preferred to give maximum increase in refractive index. In a particularly preferred reaction, the aryl polysiloxane is reacted with iodine in the presence of an aryl iodonium salt, for example (bis(trifluoroacetoxy)iodo)benzene PhI $(OOCCF_3)_2$ or diacetoxyphenyl iodine $PhI(OOCCH_3)_2$. The reaction is preferably carried out in a halogenated solvent such as $CH_2Cl_2$.

We have found that when an aryl T resin containing Ar'SiO3/2 units is reacted with chlorine, bromine or iodine, and particularly when it is reacted with iodine in the presence of an aryl iodonium salt, some SiO4/2 units are formed in addition to Ar'SiO3/2 units. This is generally advantageous, since the SiO4/2 units improve the processability and thermomechanical properties of the polysiloxane as described above. In a particularly preferred process, at least 20%, and most preferably at least 50%, of the Ar'SiO3/2 units are converted to ArSiO3/2 units, where Ar is an aryl group substituted by at least one iodine, bromine or chlorine atom, and at least 10%, most preferably at least 20%, of the Ar'SiO3/2 units are converted to SiO4/2 units. Such a degree of conversion can be obtained by reacting the aryl T resin with 30-300% by weight iodine and 50-500% by weight of the aryl iodonium salt at a temperature in the range 0-100° C., preferably ambient temperature of about 15-30° C.

A high refractive index polysiloxane can alternatively be prepared by a process in which at least one chlorosilane of the formula (Ar)m-(A)n(R)xSiCl(3-x), where Ar, A, m and n are defined as in Claim 1; each R independently represents an alkyl, aryl, alkenyl, substituted alkyl, alkoxy or hydrogen group; and x=0, 1 or 2; is hydrolysed and condensed, optionally together with another chlorosilane, in the presence of water and preferably also a dipolar aprotic solvent such as tetrahydrofuran or a ketone containing 4 to 7 C atoms (Ar)m-(A)nSiO3/2 such as methyl isobutyl ketone. Preferably the chlorosilane is a trichlorosilane (Ar)m-(A)nSiCl3 leading to a polysiloxane comprising (Ar)m-(A)nSiO3/2 units, but a dichlorosilane, a monochlorosilane and/or SiCl4 can additionally be present to introduce D, M and/or Q units. If substituted alkyl groups are present, they can be haloalkyl, particularly chloroalkyl, bromoalkyl or iodoalkyl, groups, or can for example be alkyl groups substituted by a reactive functional group such as epoxide or amino groups.

A process according to the invention for the preparation of a chlorosilane of the formula (Ar)m-(A)n(R')xSiCl(3-x), where Ar, A, m and n are defined as above; each R' independently represents an alkyl, aryl, or haloalkyl group; and x=0, 1 or 2; comprises reacting an organic chloride of the formula (Ar)m-(A)nCl with a chlorosilane of the formula H(R')xSiCl(3-x) in the presence of a tertiary amine, for example a trialkylamine such as triethylamine or tripropylamine. The organic chloride and chlorosilane are preferably used in approximately equimolar amounts or with an excess of trichlorosilane, for example a molar ratio of organic chloride to trichlorosilane of 1:0.8-3.0. The tertiary amine is preferably used in at least an approximately equimolar amount to the organic chloride; the tertiary amine is converted to its hydrochloride salt in the reaction. The reaction is preferably carried out at a temperature in the range 100-200° C. For example a trichlorosilane (Ar)m-(A)nSiCl3 useful in preparing high refractive index T resins according to the invention can be prepared by the reaction of (Ar)m-(A)nCl with HSiCl3 in the presence of a trialkylamine. Such trichlorosilanes (Ar)m-(A)nSiCl3 are new compounds.

While a high refractive index polysiloxane containing (Ar)m-(A)nSiO3/2 units and SiO4/2 units can be prepared by co-condensation of (Ar)m-(A)nSiCl3 and SiCl4, a preferred process according to the invention involves the conversion of HSiO3/2 units into Q groups. In this process for the preparation of a high refractive index polysiloxane, an aryl hydrosiloxane resin containing (Ar)m-(A)n(R)xSiO(3-x/2) units and HSiO3/2 units is treated with a base to condense at least some of the HSiO3/2 units to form SiO4/2 units. The aryl hydrosiloxane resin containing (Ar)m-(A)nSiO3/2 and HSiO3/2 units can be prepared by reaction of the chlorosilanes (Ar)m-(A)n-SiCl3 and HSiCl3 in the presence of water and a dipolar aprotic solvent.

One preferred base is a solution of an alkali metal salt of a weak acid such as a carboxylic acid, for example sodium acetate, sodium hydrogen phosphate or sodium tetraborate. An aqueous and/or organic solvent solution can be used. A preferred solvent mixture comprises water and a dipolar aprotic solvent which is at least partially miscible with water. The dipolar aprotic solvent can for example be a ketone having 4 to 7 carbon atoms such as methyl isobutyl ketone (MIBK), methyl ethyl ketone or methyl isoamyl ketone, or can be a cyclic ether such as tetrahydrofuran or dioxane. Alternatively the base may comprise an amine, preferably a tertiary amine, particularly a trialkyl amine such as triethylamine or tripropylamine, or alternatively pyridine or dimethylaminopropanol. The base can for example be an aqueous solution of triethylamine. A tertiary amine can act as both base and as a dipolar aprotic solvent, so that one base reagent comprises a solution of an alkali metal salt of a weak acid in a solvent mixture of water and a tertiary amine.

The degree of conversion of HSiO3/2 units to SiO4/2 units can be controlled by controlling the strength and concentration of the base used to treat the resin, the time of contact between the resin and the base and the temperature of the reaction. The base strength and concentration and time and temperature of treatment are preferably sufficient to condense at least 30% of the HSiO3/2 units to SiO4/2 units. In some cases 100% conversion may be desired; in other cases a lower level, for example 40-80% conversion, may be preferred. For example, a 0.5M sodium acetate solution in aqueous MIBK will cause 50% conversion of HSiO3/2 units to SiO4/2 units at 100-110° C. in about 1 hour. A 0.5M solution of sodium acetate in aqueous triethylamine will cause 50% conversion at 25° C. in about 30-40 minutes. 100% conversion can be achieved by using the latter solution at 70° C. for a few hours.

The high refractive index polysiloxane can be used in a variety of uses, for example optical uses like antireflective coatings for display devices, intra-ocular and optical lenses, optical amplifying fibres, waveguides, particularly for optical telecommunications, high refractive index adhesives or for cosmetic application, for example hair care composition with enhanced shine.

A high refractive index layer can be formed on a substrate by coating the substrate with a high refractive index polysiloxane according to the invention and curing the coating. Various methods of curing can be used. If the high refractive index polysiloxane contains Si—H groups, it can be cured by reaction with a curing agent containing alkenyl groups, for example vinyl or hexenyl groups, in the presence of a hydrosilylation catalyst such as a platinum-containing catalyst. Similarly if the high refractive index polysiloxane contains alkenyl groups it can be cured by a curing agent containing Si—H groups, or a high refractive index polysiloxane containing Si—H groups and a high refractive index polysiloxane containing alkenyl groups can be cured together. If the high refractive index polysiloxane contains reactive organic groups such as epoxide or amino groups, these can be used for curing. For example epoxide groups can be crosslinked by a polyamine, optionally using heat or UV radiation to accelerate curing, and amino groups can be crosslinked by a polyepoxide or polyisocyanate. The high refractive index polysiloxanes prepared by the processes described above frequently have sufficient Si—OH groups to undergo condensation cure, preferably in the presence of a zinc catalyst and/or at elevated temperature such as 100-300° C.

A high refractive index article can be produced by forming a high refractive index polysiloxane according to the invention into an article and curing the article.

The invention is illustrated by the following examples.

EXAMPLE 1

10.2 g of $I_2$ was added into a mixture consisting of 9.0 g $T^{Ph}$ resin, prepared by hydrolysis-condensation of $PhSiCl_3$ in a one-phase dioxane system, 18.94 g of bis(trifluoroacetoxy) iodobenzene, and 100 ml of $CH_2Cl_2$. The mixture was kept constantly stirred for 4hr at room temperature until the purple colour of iodine was fading into a light red colour. $CH_2Cl_2$ solvent was exchanged for MIBK solvent by stripping one third and addition of 100 ml MIBK, then re-stripping another one third and addition of another 50 ml more MIBK. The MIBK solution was washed with sodium bisulphate, and four times with water. Residual water was removed by use of a Dean-Stark apparatus to get after solvent stripping 23.5 g of a white soluble solid.

Iodinated phenyl and partial Si—$C_{ar}$ cleavage were observed by $^{29}$Si and $^{13}$C NMR. The formula of the resin determined by NMR spectroscopy is $T^{Ph(I)}_{0.75}Q_{0.25}$.

The highly soluble $T^{Ph(I)}_{0.75}Q_{0.25}$ resin was spin-coated onto silicon wafers and RI was evaluated by spectrometric ellipsometry (Woollam, 633 nm; this method was also used in Examples 2-5 below) after curing at 150° C. A high RI of 1.661 was observed on average over five specimens with a RI deviation below 1%.

EXAMPLE 2

2.55 g of $I_2$ was added into a mixture consisting of 3.21 g of a $T^{Ph}_{0.7}T^{Pr}_{0.3}$ phenyl propyl T resin sold under the Trade Mark 'Dow Corning Z-6018', 4.74 g of bis(trifluoroacetoxy) iodobenzene, 20 ml of $CCl_4$ and 50 ml of $CH_2Cl_2$. The reaction was kept 3 hr at room temperature, under constant stirring, until the purple colour of iodine totally disappeared. The solvents were exchanged to MIBK by stripping one third, addition of 50 ml MIBK, then stripping another third followed by addition of 50 ml more MIBK. The organic solution was washed four times with water prior to removal of residual water using a Dean-Stark apparatus. The MIBK solvent was then stripped under vacuum leading to 5.4 g of a white soluble solid.

$^{13}$C NMR revealed that 1.0 to 1.3 aromatic carbons in average have been iodinated. $^{29}$Si NMR again showed partial Si—$C_{ar}$ cleavage leading to Q sub-units formation. The formula of the resin determined by NMR spectroscopy is $T^{Ph(I)}_{0.34}T^{Pr}_{0.31}Q_{0.35}$.

The soluble $T^{Ph(I)}_{0.34}T^{Pr}_{0.31}Q_{0.35}$ resin was spin-coated onto silicon wafers and RI was evaluated after curing at 150° C. A high RI of 1.691 was observed on average over four specimens with a RI deviation below 1%.

EXAMPLE 3

(i) Preparation of Trichlorosilymethylanthracene 3.16 g of tri-n-propylamine (0.022 mol) were added into a mixture consisting of 5 g of chloromethylanthracene (0.022 mol) and 4.48 g of trichlorosilane (0.033 mol). The above mixture was refluxed at 150° C. for 72 hr. 100 ml of diethyl ether was used to extract the soluble fraction. After filtration of the insoluble salt and evaporation of the solvent, 6.8 g of a light yellow solid was obtained (85% yield). $^{29}$Si and $^{13}$C NMR and MS (mass spectroscopy) characterisation confirmed the formation of trichlorosilymethylanthracene (AnSiCl3) according to the following reaction:

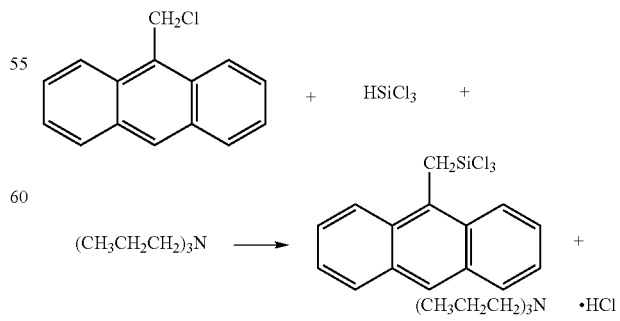

(ii). Preparation of Anthracenemethyl Silsesquioxane Resin.

3 g AnSiCl3 dissolved into 10 ml of MIBK was added dropwise into a mixture consisting of 5 ml H₂O and 10 ml MIBK at room temperature (the temperature of the reaction mixture raised to 50 to 60° C.). The mixture was refluxed at 120° C. for another 2 hours under constant stirring. The organic layer was separated and washed four times with water until neutral pH. Removal of residual water by anhydrous NaSO₄, and stripping off the solvent led to 3.8 g of a light yellow waxy material, which was highly soluble in common organic solvents such as toluene and MIBK.

By $^{29}$Si NMR, only three peaks were observed in the T regions at −53.6, −62.4 and −72.7 ppm, corresponding, respeectively, to $T_1, T_2, T_3$, species, confirming that no Si—C bond cleavage occurred during the resin formation as revealed by $^{29}$Si NMR and that the resin consisted essentially of $AnSiO_{3/2}$ units.

This resin was spin-coated onto silicon wafers and refractive index RI was evaluated after curing at 150° C. A high RI of 1.724 was observed on average over four specimens with a RI deviation below 1%.

EXAMPLE 4

(i) Preparation of 2-Iodophenylmethyltrichlorosilane.

5.67 g of tri-n-propylamine (0.040 mol) were added into a mixture consisting of 10.00 g of 1-chloromethyl-2-iodo-benzene (0.04 mol) and 8.05 g of trichlorosilane (0.060 mol). The above mixture was refluxed at 140 ° C. for 72 hr. 100 ml of diethyl ether was used to extract the soluble fraction. After filtration of the insoluble salt and evaporation of the solvent, 13 g of a light cream colour solid was obtained (92.5% yield). $^{29}$Si, $^{13}$C and $^1$H NMR characterisation confirmed the formation of 2-iodobenzyltrichlorosilane (BzISiCl3) according to the following reaction:

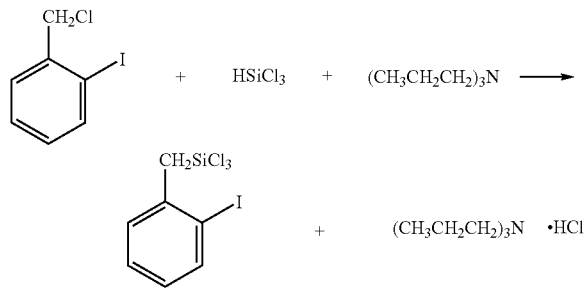

(ii) Preparation of 2-Iodophenylmethyl Silsesquioxane Resin.

6 g BzISiCl3 dissolved in 20 ml of MIBK was added dropwise into a mixture consisting of 10 ml H₂O and 20 ml MIBK at room temperature. The temperature of the reaction mixture rose to 50 to 60° C. The mixture was refluxed at 100° C. for another 1 hour under constant stirring. The organic layer was separated and washed four times with water until neutral pH. Removal of residual water by anhydrous NaSO₄, and stripping off the solvent led to 7.2 g of a light yellow solid, which was highly soluble in common organic solvents such as toluene and MIBK.

By $^{29}$Si NMR, mainly two peaks were observed in the T regions at −62.0 and −71.7 ppm, corresponding, respectively, to $T_2$ and $T_3$ species. Si—C bond cleavage occurred during the resin preparation leading to the formation of Q species as revealed by $^{29}$Si NMR. The formula of the resin determined by NMR spectroscopy is $T^{BzI}_{0.87}Q_{0.13}$.

This resin was spin-coated onto silicon wafers and refractive index RI was evaluated after curing at 150° C. A high RI of 1.644 was observed on average over four specimens with a RI deviation below 1%

EXAMPLE 5

(i) Preparation of Naphthalenemethyltrichlorosilane.

40.4 g of tri-n-propylamine (0.282 mol) were added into a mixture consisting of 50.0 g of 1-chloromethylnaphthalene (0.282 mol) and 57.3 g of trichlorosilane (0.423 mol). The above mixture was refluxed at 140° C. for 48 hr. 200 ml of diethyl ether was used to extract the soluble fraction. After filtration of the insoluble salt and evaporation of the solvent, 75 g of a brown colour solid was obtained $^{29}$Si, $^{13}$C and $^1$H NMR characterisation confirmed the formation of naphthalenemethyltrichlorosilane (NapSiCl3) according to the following reaction:

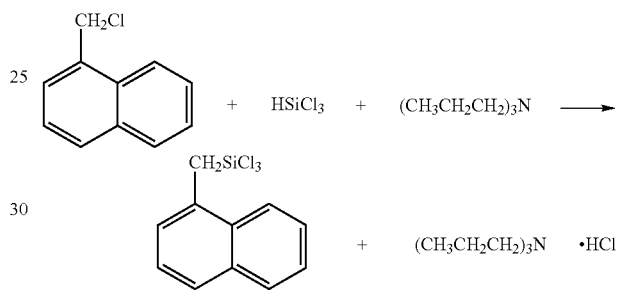

(ii) Preparation of Naphthalenemethyl Silsesquioxane Resin.

10 g NapSiCl3 dissolved in 30 ml of MIBK was added dropwise into a mixture consisting of 10 ml H₂O and 30 ml MIBK at room temperature (the temperature of the reaction mixture raised to 50 to 60° C.). The mixture was refluxed at 110° C. for another 3 hours under constant stirring. The organic layer was separated and washed four times with water until neutral pH. Removal of residual water by anhydrous NaSO₄, and stripping off the solvent led to 6.2 g of a light yellow wax, which was highly soluble in toluene and MIBK.

By $^{29}$Si NMR, mainly two peaks were observed in the T regions at −61.3 and −70.7 ppm, corresponding, respectively, $T_2$ and $T_3$ species as revealed by $^{29}$Si NMR. during the resin preparation leading to the formation of Q species as revealed by $^{29}$Si NMR. The formula of the resin determined by NMR spectroscopy is $T^{NaP}_{0.77}Q_{0.23}$.

This resin was spin-coated onto silicon wafers and refractive index RI was evaluated after curing at 150° C. A high RI of 1.643 was observed on average over four specimens with a RI deviation below 1%.

EXAMPLES 6 TO 9

18 g of AnSiCl₃ (0.055 mol) and 7.49 g of HSiCl₃ (0.055 mol) were mixed into 60 ml MIBK and added dropwise into a mixture of 60 ml H₂O, 60 ml MIBK and 40 ml Toluene over 30 minutes at room temperature. The temperature of the reaction mixture rose to 60° C. upon addition. The reaction mixture was refluxed at 110° C. for further 2hr. The organic layer was separated and washed four times with distilled water until neutral. A first portion (40 ml) of the resulting $T^{An}T^{H}$ resin (which also contained some Q groups) was sampled from the solution. Removal of residual water and stripping of the solvent led to 5.0 g of a light brown solid. (Example 6)

The rest of the $T^{An}T^H$ solution was mixed with 100 ml of 0.5M aqueous sodium acetate (NaAc) solution at 40° C. Different compositions of $T^{An}T^HQ$ were then sampled (40 ml each) out of the organic layer from the solution system at different times as shown in Table 1 below. After washing the samples four times, stripping off the residual water and solvent, approximately 4 to 5 g. of a light brown solid were obtained from each of these portions. (Examples 7 to 9)

TABLE 1

| | Reaction time | % of $T^H$ conversion | Formula (by $^{29}$Si NMR) |
|---|---|---|---|
| Example 6 | 0 hr | 27.3 | $T^{An}_{0.45}T^H_{0.40}Q_{0.15}$ |
| Example 7 | 1 day | 50.0 | $T^{An}_{0.45}T^H_{0.28}Q_{0.28}$ |
| Example 8 | 3 day | 61.8 | $T^{An}_{0.45}T^H_{0.21}Q_{0.34}$ |
| Example 9 | 6 days | 70.7 | $T^{An}_{0.45}T^H_{0.16}Q_{0.39}$ |

These $T^{An}T^HQ$ resins were each spin-coated onto silicon wafers and refractive index RI was evaluated by spectroscopic ellipsometry (Rudolph, 633 nm) of two specimens after curing at 150° C. High RIs between 1.647 and 1.704 were observed, as listed in Table 2, with a RI deviation below 1% for each example

TABLE 2

| | Compositions | RI |
|---|---|---|
| Example 6 | $T^{An}_{0.45}T^H_{0.40}Q_{0.15}$ | 1.647 |
| Example 7 | $T^{An}_{0.45}T^H_{0.28}Q_{0.28}$ | 1.692 |
| Example 8 | $T^{An}_{0.45}T^H_{0.21}Q_{0.34}$ | 1.702 |
| Example 9 | $T^{An}_{0.45}T^H_{0.16}Q_{0.39}$ | 1.704 |

EXAMPLES 10 TO 13

20.00 g of BzISiCl$_3$ (0.057 mol) and 7.71 g of HSiCl$_3$ (0.057 mol) were mixed into 40 ml MIBK and added dropwise into a mixture of 60 ml H$_2$O, 80 ml MIBK and 40 ml Toluene over 30 minutes at room temperature. The temperature of the reaction mixture rose to 60° C. upon addition. The reaction mixture was refluxed at 100° C. for further 2 hr. The organic layer was separated and washed four times with distilled water until neutral. A first portion (40 ml) of the resulting $T^{BzI}T^H$ resin (which also contained some Q groups) was sampled from the solution. Removal of residual water and stripping of the solvent led to 5.0 g of a crispy white solid. (Example 10).

The rest of the $T^{BzI}T^H$ solution was mixed with 100 ml of 0.5M aqueous sodium acetate (NaAc) solution at 40° C. Different compositions of $T^{BzI}T^HQ$ were then sampled (40 ml each) out of the organic layer from the solution system at different times as shown in Table 3 below. After washing the samples four times, stripping off the residual water and solvent, approximately 4 to 5 g. of a crispy white solid were obtained from each of these portions. (Examples 11 to 13)

TABLE 3

| | Reaction time | % of $T^H$ conversion | Formula (by $^{29}$Si NMR) |
|---|---|---|---|
| Example 10 | 0 hr | 26.0 | $T^{BzI}_{0.50}T^H_{0.37}Q_{0.13}$ |
| Example 11 | 6 hr | 40.8 | $T^{BzI}_{0.51}T^H_{0.29}Q_{0.20}$ |
| Example 12 | 1 day | 54.0 | $T^{BzI}_{0.51}T^H_{0.23}Q_{0.27}$ |
| Example 13 | 6 days | 80.0 | $T^{BzI}_{0.50}T^H_{0.10}Q_{0.40}$ |

The $T^{BzI}T^HQ$ resins of Examples 10 to 12 were each spin-coated onto silicon wafers and refractive index RI was evaluated by spectroscopic ellipsometry (Rudolph, 633 nm; average of 2 specimens) after curing at 150° C. A high RI between 1.612 and 1.625 was observed as shown in Table 4 with a RI deviation below 1% for each example

TABLE 4

| Ref | Compositions | RI |
|---|---|---|
| Example 10 | $T^{BzI}_{0.50}T^H_{0.37}Q_{0.13}$ | 1.625 |
| Example 11 | $T^{BzI}_{0.51}T^H_{0.29}Q_{0.20}$ | 1.612 |
| Example 12 | $T^{BzI}_{0.51}T^H_{0.23}Q_{0.27}$ | 1.622 |

EXAMPLES 14 TO 16

30.00 g of NapSiCl$_3$ (0.109 mol) and 14.72 g of HSiCl$_3$ (0.109 mol) were mixed into 60 ml MIBK and added dropwise into a mixture of 90 ml H$_2$O, 120 ml MIBK and 60 ml Toluene over 40 minutes at room temperature. The temperature of the reaction mixture rose to 60° C. upon addition. The reaction mixture was refluxed at 100° C. for further 2 hr. The organic layer was separated and washed four times with distilled water until neutral. A first portion (100 ml) of the resulting $T^{Nap}T^H$ resin (which also contained some Q groups) was sampled from the solution. Removal of residual water and stripping of the solvent led to 10.1 g of a light yellow solid. (Example 14)

The rest of the $T^{Nap}T^H$ solution was mixed with 100 ml of 0.5M aqueous sodium acetate (NaAc) solution at 25° C. Different compositions of $T^{Nap}T^HQ$ were then sampled (70 ml each) out of the organic layer from the solution system at two different times as shown in Table 5 below. After washing the samples four times, stripping off the residual water and solvent, approximately 7.5 and 8.0 g of light yellow solid were obtained from each of these portions. (Examples 15 and 16)

TABLE 5

| | Reaction time | % of $T^H$ conversion | Formula (by $^{29}$Si NMR) |
|---|---|---|---|
| Example 14 | 0 hr | 40.0 | $T^{Nap}_{0.49}T^H_{0.30}Q_{0.20}$ |
| Example 15 | 1 day | 44.0 | $T^{Nap}_{0.50}T^H_{0.28}Q_{0.22}$ |
| Example 16 | 7 day | 56.9 | $T^{Nap}_{0.49}T^H_{0.22}Q_{0.29}$ |

These $T^{Nap}T^HQ$ resins were each spin-coated onto silicon wafers and refractive index RI was evaluated by spectroscopic ellipsometry (Rudolph, 633 nm; average of two specimens) after curing at 150° C. The results are listed in Table 6.

TABLE 6

| Ref | Compositions | RI |
|---|---|---|
| Example 14 | $T^{Nap}_{0.49}T^H_{0.30}Q_{0.20}$ | 1.608 |
| Example 15 | $T^{Nap}_{0.50}T^H_{0.28}Q_{0.22}$ | 1.586 |
| Example 16 | $T^{Nap}_{0.49}T^H_{0.22}Q_{0.29}$ | 1.581 |

EXAMPLE 17

Preparation of Iodinated Methylanthracene Resin 2.34 g of I$_2$ was added into a mixture consisting of 1.5 g of $T^{An}$resin, 3.97 g of bis(trifluoroacetoxy)iodo-benzene, and 50 ml of CH$_2$Cl$_2$. The mixture was kept constantly stirred at room temperature until the purple colour of iodine was fading into a deep green colour. $CH_2Cl_2$ solvent was exchanged for MIBK solvent by stripping one third and addition of 100 ml MIBK, then re-stripping another one third and addition of another 50 ml more MIBK. The MIBK solution was washed with sodium bisulphate, and four times with water. Residual water was removed by use of a Dean-Stark apparatus to get after solvent stripping 2.0 g of a deep brown soluble powder.

Iodinated methylanthracene and partial Si—$C_{ar}$ cleavage were observed by $^{29}Si$ and $^{13}C$ NMR. The average formula of the resin determined by NMR spectroscopy is $T^{An(I)n}_{0.38}Q_{0.62}$ (I<n<3).

The iodinated $T^{An(I)n}_{0.38}Q_{0.62}$ resin was spin-coated onto silicon wafers and RI was evaluated by spectrometric ellipsometry (Woollam, 633 nm) after curing at 150° C. A high RI of 1.770 was observed.

The invention claimed is:

1. A polysiloxane having a refractive index of at least 1.581 measured at light wavelength 633 nm, which polysiloxane includes siloxane T units of the formula:

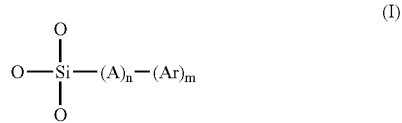

(I)

where A represents an alkylene group having 1 to 4 carbon atoms; n=0 or 1; m is at least 1; and Ar is a polynuclear aromatic group substituted by at least one iodine, bromine or chlorine atom, wherein at least 20% of the siloxane units of the resin are of formula (I), and wherein at least 5% of the siloxane units of the resin are SiO4/2 units, provided said polysiloxane is substantially free of M and D units.

2. A polysiloxane according to claim 1 in which at least 10% of the siloxane units of the resin are SiO4/2 units.

3. A polysiloxane according to claim 1 in which the polysiloxane also contains curable groups selected from the group consisting of alkenyl groups, Si—H groups, epoxyalkyl groups, aminoalkyl groups, and Si—OH groups.

4. A process for producing a high refractive index article comprising forming a high refractive index polysiloxane as claimed in claim 1 into an article and curing the article.

5. A polysiloxane according to claim 1 in which n is 1, A has more than 1 carbon atom, m is at least 2.

6. A polysiloxane according to claim 1 in which n is 0 for at least 50% of the siloxane units of formula (I) and n is 1 for up to 50% of the siloxane units of formula (I) in the resin.

7. A process for forming a high refractive index layer on a substrate comprising coating the substrate with a high refractive index polysiloxane and curing the coating, the high refractive index polysiloxane having a refractive index of at least 1.58 1 measured at light wavelength 633 nm, and which high refractive index polysiloxane includes siloxane T units of the formula:

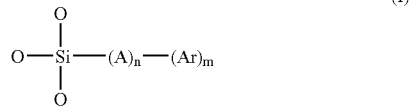

(I)

where A represents an alkylene group having 1 to 4 carbon atoms; n=0 or 1; m is at least 1; and Ar is selected from the group consisting of (i) an aryl group substituted by at least one halogen selected from the group consisting of iodine, bromine and chlorine atom, and (ii) a polynuclear aromatic group, wherein at least 20% of the siloxane units of the resin are of formula (I), and wherein at least 5% of the siloxane units of the resin are SiO4/2 units, provided the polysiloxane is substantially free from M and D units.

8. A process according to claim 7 in which Ar is an optionally substituted naphthyl, anthracenyl, phenanthrenyl or pyrenyl group.

9. A process according to claim 7 in which Ar is a polynuclear aromatic group substituted by at least one iodine, bromine or chlorine atom.

10. A process according to claim 7 in which Ar is a phenyl group substituted by at least one iodine atom.

11. A process according to claim 7 in which Ar is an optionally substituted polynuclear group having non-fused aromatic rings.

12. A process according to claim 7 in which at least 10% of the siloxane units of the resin are SiO04/2 units.

13. A process according to claim 7 in which the polysiloxane also contains curable groups selected from the group consisting of alkenyl groups, Si—H groups, epoxyalkyl groups, aminoalkyl groups, and Si—OH groups.

14. A process according to claim 7 in which n is 1, A has more than 1 carbon atom, m is at least 2.

15. A process according to claim 7 in which n is 0 for at least 50% of the siloxane units of formula (I) and n is 1 for up to 50% of the siloxane units of formula (I) in the resin.

16. A polysiloxane having a refractive index of at least 1.581 measured at light wavelength 633 nm, which polysiloxane includes siloxane T units of the formula:

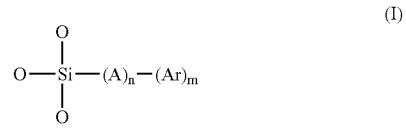

(I)

where A represents an alkylene group having 1 to 4 carbon atoms; n=0 or 1; m is at least 1; and Ar is a phenyl group substituted by at least one iodine atom, wherein at least 20% of the siloxane units of the resin are of formula (I), and wherein at least 5% of the siloxane units of the resin are SiO4/2 units, provided said polysiloxane is substantially free of M and D units.

17. A polysiloxane according to claim 16 in which at least 10% of the siloxane units of the resin are SiO4/2 units.

18. A polysiloxane according to claim 16 in which the polysiloxane also contains curable groups selected from the group consisting of alkenyl groups, Si—H groups, epoxyalkyl groups, aminoalkyl groups, and Si—OH groups.

19. A polysiloxane according to claim 16 in which n is 1, A has more than 1 carbon atom, m is at least 2.

20. A polysiloxane according to claim 16 in which n is 0 for at least 50% of the siloxane units of formula (I) and n is 1 for up to 50% of the siloxane units of formula (I) in the resin.

21. A process for producing a high refractive index article comprising forming a high refractive index polysiloxane as claimed in claim 16 into an article and curing the article.

22. A substrate including a coating formed thereon from a cured high refractive index polysiloxane, said high refractive index polysiloxane having a refractive index of at least 1.581 measured at light wavelength 633 nm, and which high refractive index polysiloxane includes siloxane T units of the formula:

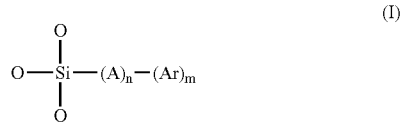

where A represents an alkylene group having 1 to 4 carbon atoms; n=0 or 1; m is at least 1; and Ar is selected from the group consisting of (i) an aryl group substituted by at least one halogen selected from the group consisting of iodine, bromine and chlorine atom, and (ii) a polynuclear aromatic group, wherein at least 20% of the siloxane units of the resin are of formula (I), and wherein at least 5% of the siloxane units of the resin are $SiO_{4/2}$ units, provided said polysiloxane is substantially free of M and D units.

23. A substrate including a coating formed thereon according to claim 22 in which at least 10% of the siloxane units of the resin are $SiO_{4/2}$ units.

24. A substrate including a coating formed thereon according to claim 22 in which Ar is an optionally substituted naphthyl, anthracenyl, phenanthrenyl or pyrenyl group.

25. A substrate including a coating formed thereon according to claim 22 in which Ar is a polynuclear aromatic group substituted by at least one iodine, bromine or chlorine atom.

26. A substrate including a coating formed thereon according to claim 22 in which Ar is a phenyl group substituted by at least one iodine atom.

27. A substrate including a coating formed thereon according to claim 22 in which the polysiloxane also contains curable groups selected from the group consisting of alkenyl groups, Si—H groups, epoxyalkyl groups, aminoalkyl groups, and Si—OH groups.

28. A substrate including a coating formed thereon according to claim 22 in which Ar is an optionally substituted polynuclear group having non-fused aromatic rings.

29. A substrate including a coating formed thereon according to claim 22 in which n is 1, A has more than 1 carbon atom, m is at least 2.

30. A substrate including a coating formed thereon according to claim 22 in which n is 0 for at least 50% of the siloxane units of formula (I) and n is 1 for up to 50% of the siloxane units of formula (I) in the resin.

* * * * *

UNITED STATES PATENT AND TRADEMARK OFFICE
CERTIFICATE OF CORRECTION

PATENT NO. : 7,429,638 B2  Page 1 of 1
APPLICATION NO. : 10/486375
DATED : September 30, 2008
INVENTOR(S) : Chevalier et al.

It is certified that error appears in the above-identified patent and that said Letters Patent is hereby corrected as shown below:

In Column 11, line 56, please delete "1.58 1" and replace with -- 1.581 --.

In Column 12, line 25, please delete "SiO04/2" and replace with -- SiO4/2 --.

Signed and Sealed this

Second Day of June, 2009

JOHN DOLL
*Acting Director of the United States Patent and Trademark Office*